United States Patent [19]
Fesus et al.

[11] Patent Number: 5,750,360
[45] Date of Patent: May 12, 1998

[54] METHOD FOR QUANTITATIVELY MEASURING APOPTOSIS

[75] Inventors: Laszlo Fesus, Debrecen Nagyerdei, Hungary; Mauro Piacentini, Rome, Italy

[73] Assignee: LXR Biotechnology Inc., Richmond, Calif.

[21] Appl. No.: 484,339

[22] Filed: Jun. 7, 1995

[51] Int. Cl.$^6$ .............................. C12Q 1/37; C12Q 1/48; C12P 21/06; G01N 33/00

[52] U.S. Cl. .............................. 435/23; 435/24; 435/15; 435/4; 435/26; 435/68.1; 435/110; 435/115; 436/63; 436/86; 436/89; 530/300; 530/322; 426/656

[58] Field of Search .................... 435/23, 24, 15, 435/4, 68.1, 26, 110, 115; 436/63, 86, 89; 530/300, 322; 426/656

[56] References Cited

U.S. PATENT DOCUMENTS

| | | | |
|---|---|---|---|
| 4,167,449 | 9/1979 | Gargiulo et al. | 435/24 |
| 4,191,808 | 3/1980 | Nagatsu et al. | 435/23 |
| 4,808,741 | 2/1989 | Oudenes | 435/23 |
| 4,935,526 | 6/1990 | Bres et al. | 435/23 |
| 4,940,662 | 7/1990 | Yamazaki et al. | 435/68.1 |
| 5,037,207 | 8/1991 | Tomei et al. | 356/444 |
| 5,330,972 | 7/1994 | Cope | 435/23 |

FOREIGN PATENT DOCUMENTS

WO 93/20195  10/1993  WIPO.

OTHER PUBLICATIONS

Wyllie, "Glucocortoid–induced thymocyte apoptosis is associated with endogenous endonuclease activation" *Nature* (1980) 284:555–556.

Kanter et al., "Epidermal growth factor and tumor promoters prevent DNA fragmentation by different mechanisms" *Biochem. Biophys. Res. Comm.* (1984) 118:392–399.

Duke et al., "IL–2 addiction: Withdrawal of growth factor activates a suicide program in dependent T cells" *Lymphotine Res.* (1986) 5:289–299.

Tomei et al., "Inhibition of radiation–induced apoptosis in vitro by tumor promoters" *Biochem. Biophys. Res. Comm.* (1988) 155:324–331.

Kruman et al., "Apoptosis of murine BW 5147 thymoma cells induced by dexamethasone and γ–irradiation" *J. Cell. Physiol.* (1991) 148:267–273.

Ameisen et al., "Cell dysfunction and depletion in AIDS: The programmed cell death hypothesis" *Immunol. Today* (1991) 12:102–105.

Sheppard et al., "The relationship between AIDS and immunologic tolerance" *J. AIDS* (1992) 5:143–147.

Vermes et al., "Apoptosis and programmed cell death in health and disease" *Advances in Clinical Chemistry* vol. 31, Spiegel, H.E., ed., (1994) Academic Press, New York. The title page and table of contents are included herewith.

Gerschenson et al., "Apoptosis: A different type of cell death" *FASEB J.* (1992) 6:2450–2455.

Cohen et al., "Apoptosis and programmed cell death in immunity" *Ann. Rev. Immunol.* (1992) 10:267–293.

Greenberg et al., "Transglutaminases: Multifunctional cross–linking enzymes that stabilize tissues" *FASEB J.* (1991) 6:3071–3077.

Piacentini et al., "Tissue transglutaminase in cells undergoing apoptosis" *Apoptosis II: The Molecular Basis of Apoptosis in Disease*, Current Communications in Cell & Molecular Biology 8, (1994) Cold Spring Laboratory Press, New York, pp. 143–163.

(List continued on next page.)

*Primary Examiner*—Louise Leary
*Attorney, Agent, or Firm*—Morrison & Foerster

[57] ABSTRACT

The invention encompasses methods of detecting and/or quantifying ε(γ–glutamyl)lysine isodipeptide by catalytically releasing lysine, then measuring free lysine.

15 Claims, 6 Drawing Sheets

OTHER PUBLICATIONS

Fesus et al., "Formation of $N^\epsilon$-($\gamma$-glutamyl)-lysine isodipeptide in Chinese-hamster ovary cells" *Biochem. J.* (1989) 263:843–848.

Fesus et al., "Degradation of cells dying by apoptosis leads to accumulation of $\epsilon$($\gamma$-glutamyl)lysine isodipeptide in culture fluid and blood" *FEBS Lett.* (1991) 284:109–112.

Harsfalvi et al., "Presence and possible origin of $\epsilon$($\gamma$-glutamyl)lysine isodipeptide in human plasma" *Thrombosis & Haemostasis* (1992) 67:60–62.

Tarcsa et al., "Determination of $\epsilon$($\gamma$-glutamyl)lysine crosslink in proteins using phenylisothiocyanate derivatization and high-pressure liquid chromatographic separation" *Anal. Biochem.* (1990) 186:135–140.

Fink et al., "$\gamma$-glutamylamine cyclotransferase[1] (rabbit kidney)" *Meth. Enzymol.* (1983) 94:347–351.

Fesus et al., "Activation of transglutaminase and production of protein-bound $\gamma$-glutamylhistamine in stimulated mouse mast cells" *J. Biol. Chem.* (1985) 260:13771–13778.

Harsfalvi et al., "Enzymatic fluorimetric assay for $\epsilon$($\gamma$-glutamyl)lysine isodipeptides" *Fibrinol.* (1994) 8:378–381.

Squires et al., "Isolation, characterization and seasonal variations in the concentration of $N^\epsilon$-($\gamma$-glutamyl)-lysine isodipeptide in the blood plasma of the winter flounder (*Pseudopleuronectes americanus*)" *Biochem. J.* (1980) 185:761–766.

Motoki et al., "Crosslinking between different food proteins by transglutaminase" *J. Food Sci.* (1983) 48:561–565.

Nio et al., "Gelation of protein emulsion by transglutaminase" *Agric. Biol. Chem.* (1986) 50:1409–1412.

Friedman et al., "Nutritional Improvement of bread with lysine and $\gamma$-glutamyllysine" *J. Agric. Food Chem.* (1990) 38:2011–2020.

Nakatani et al., "Enzymic determination of L-lysine in biological materials" *Anal. Biochem.* (1972) 49:225–231.

Fosse et al., "A bioluminescence method for the measurement of L-glutamate: Applications to the study of changes in the release of L-glutamate from lateral geniculate nucleus and superior colliculus after visual cortex ablation in rats" *J. Neurochem.* (1986) 47:340–349.

Gavrieli et al., "Identification of programmed cell death in situ via specific labeling of nuclear DNA fragmentation" *J. Cell Biol.* (1992) 119:493–501.

Nicoletti et al., "A rapid and simple method for measuring thymocyte apoptosis by propidium iodide staining and flow cytometry" *J. Immunol. Meth.* (1991) 139:271–279.

SACCHAROPINEOH
α-KETOGLUTARATE ⟶ SACCHAROPINE FORMATION FROM LYSINE AND KETOGLUTARATE
NADH

NADH CONSUMPTION

BIOLUMINESCENT ASSAY OF NADH

METHOD FOR QUANTITATIVELY MEASURING APOPTOSIS

FIELD OF THE INVENTION

The invention provides methods for rapid and quantitative measurement of ε(γ-glutamyl)lysine isodipeptide bonds, both in vivo and in vitro in a wide variety of sample types. Such methods are useful for monitoring cell death associated with disease states, and efficacy of therapeutic regimens.

BACKGROUND OF THE INVENTION

Apoptosis, a naturally occurring form of programmed cell death, has become one of the major issues of current biomedical research. Apoptosis is a normal physiologic process that leads to individual cell death. Apoptosis is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death may be initiated by a wide variety of signals, including hormones, serum growth factor deprivation, chemotherapeutic agents, ionizing radiation, and infection by human immunodeficiency virus (HIV). Wyllie (1980) *Nature* 284:555–556; Kanter et al. (1984) *Biochem. Biophys. Res. Commun.* 118:392–399; Duke and Cohen (1986) *Lymphokine Res.* 5:289–299; Tomei et al. (1988) *Biochem. Biophys. Res. Commun.* 155:324–331; and Kruman et al. (1991) *J. Cell. Physiol.* 148:267–273; Ameisen and Capron (1991) *Immunol. Today* 12:102–105; Sheppard et al. (1992) *J. AIDS* 5:143–147; and Vermes et al. (1994) *Advances in Clinical Chemistry* Vol. I, Academic Press, Inc. Thus agents that affect the biological control of apoptosis have therapeutic utility in numerous clinical indications.

Apoptotic cell death is characterized by cellular shrinkage, chromatin condensation and margination, cytoplasmic blebbing, increased membrane permeability and interchromosomal DNA cleavage. Gerschenson et al. (1992) *FASEB J.* 6:2450–2455; and Cohen and Duke (1992) *Ann. Rev. Immunol.* 10:267–293. Apoptosis is associated with the formation of so-called apoptotic bodies which are ultimately phagocytosed by phagocytic cells.

In addition to apoptosis, cell death also occurs by necrosis. Necrosis is a traumatic metabolic failure resulting directly from severe molecular and/or structural damage. Necrosis is commonly marked by an early increase in total cell volume and subcellular organelle volume followed by autolysis. Nuclear changes are found to be late events and are a consequence of activation of cellular hydrolytic enzymes.

In the ordinary course of events, cells undergo apoptosis in response to signals sent by other cells indicating a need for cell replacement, or perhaps from internal signals indicating that the ongoing existence of the cell would be damaging to the organism. In certain cases, the body malfunctions and sends out aberrant apoptosis signals. These signals may cause inappropriate apoptosis resulting in severe tissue damage, or delayed apoptosis resulting in overpopulation of certain cell types or the continued existence of damaged or defective cells.

Although apoptosis has long been recognized as an inherent part of the normal life cycle of cells, the disregulation of normal and timely apoptotic cell death has only recently been found to be involved in a broad range of disease conditions. Examples of disease conditions associated with inappropriate apoptosis are heart tissue damage following a heart attack and immunosuppression-related disorders, such as acquired immune deficiency syndrome (AIDS). An example of a disease associated with delayed apoptosis is cancer.

Recent literature suggests that apoptosis is involved in a wide variety of normal and diseased states. For instance, apoptosis is thought to be responsible for deletion of T and B autoreactive lymphocytes, glucocorticoid induced lymphocyte death, cell death induced by radiation and heating, as well as cell death following deprivation of specific growth factors. Immunosuppression linked with HIV infection has been associated with a modification of apoptosis control. Cytotoxic lymphocytes induce apoptosis in target cells, and apoptosis is induced in leukemia cells by specific antibodies to cell surface antigens. Apoptosis has also been observed in preneoplastic foci in liver following promoter withdrawal, and in involuting hormone-dependent tissues and tumors upon hormone withdrawal. Some antitumor drugs, e.g. inhibitors of topoisomerase II as well as tumor necrosis factor, induce apoptotic cell death.

The observation that the disregulation of apoptosis can play a key role in the onset of, or damage caused by, such diseases creates a need to measure levels of apoptosis in patients. Currently, apoptosis is measured by, for example, direct visualization, DNA laddering, flow cytometry (propidium iodide labelling) and measuring the expression of Fas. These methods are invasive if used to determine in vivo levels of apoptosis. Each requires cell samples obtained from the area undergoing apoptosis. Furthermore, the methods are cumbersome and time consuming, and would not readily conform to high throughput assays. Commercially available kits, such as ApopTag™, sold by ONCOR (Gaithersburg, Md.) are available to detect apoptosis. These tests are suitable for the laboratory setting but do not provide a method of monitoring apoptosis in the clinical setting.

In general, transglutaminases catalyze the posttranslational modification of proteins. This is accomplished by transamidation of the available glutamine residues. As a result of this catalysis, ε(γ-glutamyl)lysine cross-links are formed and polyamines are incorporated into protein substrates. The resulting isodipeptide cross-link is relatively stable and resistant to proteolysis.

Tissue transglutaminase is a $Ca^{++}$ dependent cytoplasmic enzyme normally present in many cells. However, the enzyme is not activated by normal $Ca^{++}$ levels found in cells. Activation of the enzyme in vivo does not occur until the intracellular free $Ca^{++}$ concentration increases which typically occurs, for example, when lymphocytes undergo activation-induced apoptosis. Cells which contain tissue transglutaminases include, for example, those found on blood vessel walls. A review of transglutaminase is contained in Greenberg et al. (1991) *FASEB J.* 5:3071–3077.

Tissue transglutaminase is activated in cells undergoing apoptosis to form ε(γ-glutamyl)lysine isodipeptide bonds (hereinafter "isodipeptide") between proteins. Piacentini et al. (1994) in *Apoptosis II*, Tomei and Cope eds.; and *Current Communications in Cell & Molecular Biology* 8, Cold Spring Harbor Laboratory Press, pp. 143–163 (1994). Apoptotic cells are engulfed and degraded in the lysosomes of phagocytic cells where the cross-linked proteins are degraded. Since lysozymes lack an enzyme capable of cleaving the isodipeptide bond; the isodipeptide is not cleaved. Rather, the isodipeptide is released into the extracellular space, including blood plasma.

The isodipeptide was first found in plasma. Fesus et al. (1989) *Biochem. J.* 263:843–848; Fesus et al. (1991); *FEBS*

284:109–112; and Harsfalvi (1992) *Thromb. Haemostasis* 67:60–62. The observation that there is a reproducibly measured basal level of the isodipeptide in the circulation (humans: 1.2–2.7 μmol/L; rats: 1.8–3.2 μmol/L; mice: 1.5–2.4 μmol/L) is in agreement with the notion that a constant, basal apoptosis rate exists due to continuous cell turnover in tissues.

A technique has been developed for the quantitation of the isodipeptide released during protein digestion. This method is based on three chromatography steps, high sensitivity detection following phenylisothiocyanate (PITC) derivatization and high performance liquid chromatography (HPLC) separation and using an isotope tracer to calculate recovery. Tarcsa et al. (1990) *Anal. Biochem.* 186:135–140. Results obtained using the HPLC technique described by Tarcsa et al. (1990) demonstrated that the isodipeptide level was significantly increased in the culture fluid of a primary culture system (neonatal rat liver cells) when a wave of apoptosis and phagocytosis of dying hepatocytes was induced. Fesus et al. (1991).

A large proportion of hepatocytes die by apoptosis during the involution of rat liver which follows hyperplasia induced by the liver mitogen lead nitrate. The induction and activation of tissue transglutaminase has been shown to occur after treatment with lead nitrate. Significantly increased isodipeptide levels with peak values about five times greater than controls occur during this apoptosis clearly linking the two phenomena. Fesus et al. (1991).

There are three independent signal pathways (dexamethasone-, T cell receptor-, and p53-dependent) through which apoptosis and the induction of tissue transglutaminase can be achieved in mouse thymus in vivo. All of these stimuli lead to the involution of the thymus (disappearance of about 80% of the tissue within 24 hours) achieved by a very fast death rate and phagocytosis, then degradation of the dying cells. In all three cases, the basal level of the isodipeptide in the plasma rises to 5–8 times at 24 hours after the stimuli, then returns to normal level 2 days later. The HPLC techniques described in Tarcsa et al. (1990) were used to determine the levels of isodipeptide in the plasma samples.

It has recently been found that there is a significant rate of apoptosis of CD4$^+$ T cells in AIDS patients. Recently obtained data indicate that the rate of apoptosis of T cells is reflected in the number of peripheral T cells showing high content of tissue transglutaminase protein and in the increased level of isodipeptide in blood plasma (FIG. 1). These results were obtained using the HPLC techniques described by Tarcsa et al. (1990).

Recently, isodipeptide measurements have been obtained by an HPLC technique which in itself was an improvement as compared to previous methods. However, the HPLC technique is very time consuming, it requires three chromatography steps and the use of an internal isotope standard. Such a complicated method works in research laboratories but is not applicable for the conditions of routine clinical chemistry laboratories where simplicity, time, instrumentation and serial measurements are essential.

Several attempts have been made to develop new assays for the measurement of the isodipeptide. One such technique, a fluorimetric assay, Harsfalvi et al. (1994), is simple but not sensitive enough to make reliable measurements of low concentrations of the isodipeptide including those found in normal human plasma. It would therefore be useful to have a clinically relevant assay to detect isodipeptides in body fluids, particularly for AIDS patients.

γ-glutamylamine cyclotransferase (GACT) enzymatically hydrolyzes the isodipeptide. GACT has been purified from the rabbit kidney. Fink et al. (1983) *Meth. Enzymol.* 94:347–351. GACT was used to release free histamine from a γ-glutamyl derivative and was found to merely suggest the presence of γ-glutamyl derivative. Positive identification of γ-glutamyl histamine was accomplished by HPLC which separated histidine and γ-glutamyl histamine. Fesus et al. (1985) *J. Biol. Chem.* 260:13771–13778.

Thus, there is a need for a rapid, reproducible, quantitative method to detect in vivo levels of apoptosis in a clinical setting.

All references cited herein both supra and infra are incorporated herein by reference.

SUMMARY OF THE INVENTION

The invention encompasses methods of detecting and/or quantifying ε(γ-glutamyl)lysine isodipeptide by applying coupled enzyme reactions to release lysine and convert lysine to saccharopine in a process in which NADH is consumed. NADH consumption is then quantitated, preferably in a luminescence reaction.

BRIEF DESCRIPTION OF THE DRAWINGS

FIG. 3B depicts a reaction scheme of the saccharopine DH reaction.

DETAILED DESCRIPTION OF THE INVENTION

Figure 1A:
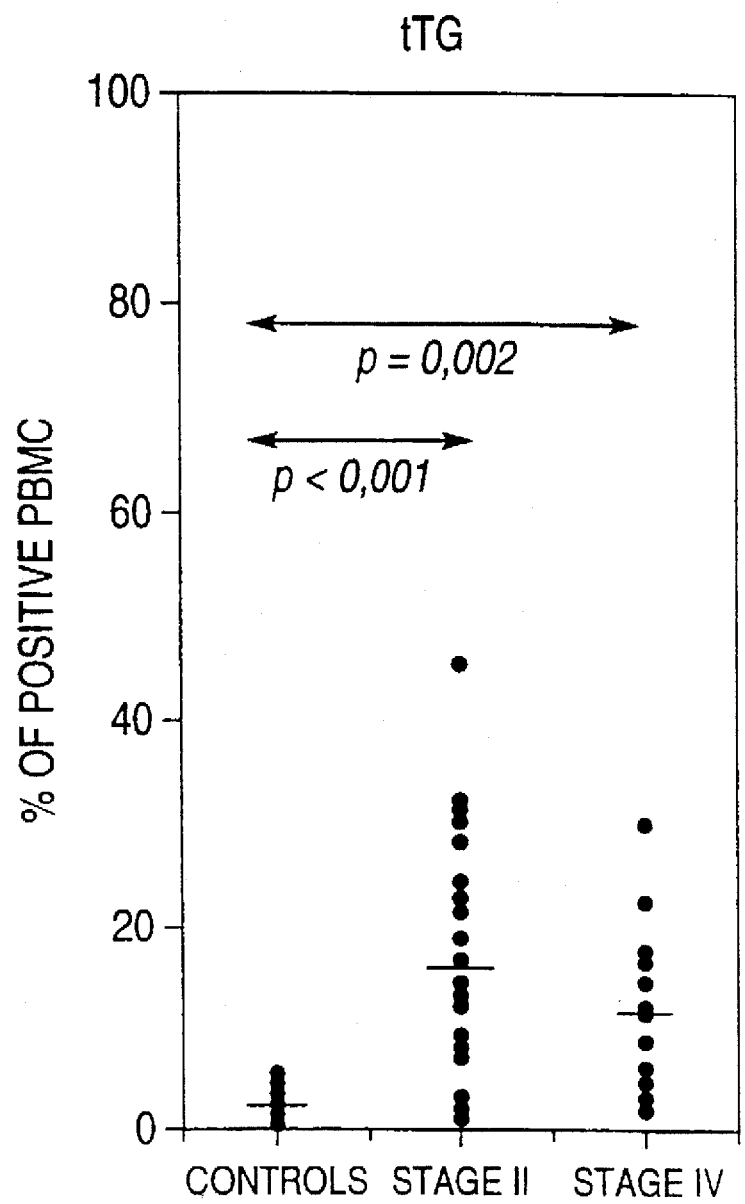
FIGS. 1A and 1B depict the increase in apoptosis in AIDS patients by (A) immunohistochemical detection of tissue transglutaminase and the Bcl-2 antiapoptosis protein in human peripheral blood lymphocytes of healthy individuals and AIDS patients, and (B) measuring isodipeptde concentration (1–5 μmol/L) in blood plasma of healthy individuals and AIDS patients.

The present invention provides methods to determine isodipeptide concentration in body fluids. The methods utilize the high sensitivity of bioluminescence measurements allowing reliable measurements in very low concentration ranges, take advantage of the wide use of luminometers in clinical laboratories, avoid complicated chromatography steps, and provide results in a relatively short period of time. The present invention provides, for the first time, a simple test to monitor in vivo tissue apoptosis rates.

In vivo apoptosis experiments using animal models are essential to understanding the biology of apoptosis, to study the involvement of apoptosis in the pathogenesis of various diseases using various animal models and to monitor the efficacy of novel therapeutic agents in animal tumor experiments. In all of these cases, the present invention serves as an easy test which can be performed without destruction of laboratory animals and, in many cases, with minimal or no invasive procedures.

The invention is useful in human studies to clarify the role of apoptosis in the pathogenesis and course of certain diseases such as cancer, AIDS and other viral infections, autoimmune diseases, thrombolysis and trauma of the central nervous system.

The level of in vivo apoptosis can be measured to determine the effectiveness of any treatment that modulates cell death. For instance, during treatment of heart attacks, the level of isodipeptide in the sera can be monitored over time to determine whether the level of apoptosis is increasing or decreasing in response to therapeutic intervention. Other suitable treatments which can be monitored include, but are not limited to, chemotherapy, radiation, inhibition of cell death due to reperfusion and prevention of cell death in virally infected patients. Types of cell death due to reperfusion include, but are not limited to, myocardial infarction and cerebrospinal damage.

The clinical efficacy of potential antiapoptotic therapeutic agents can also be assessed by administering to an animal the agent and monitoring over time the changes in the levels of the isodipeptide. Recent studies have clearly shown that most of the currently used anticancer chemotherapeutic agents induce apoptosis in the malignant cells. Similarly, optimal radiotherapy should lead to elimination of malignant cells by apoptosis. Thus, there is a need to measure levels of apoptosis induced by chemotherapy and radiation therapy, especially in view of the inaccessibility of tumors for repeated histologic examinations. The invention thus encompasses methods of monitoring the effectiveness of apoptosis induction in these cases.

The methods described herein have a variety of clinical applications. These methods are generally useful for monitoring levels of cell death, particularly that caused by apoptosis. Disorders which can be monitored involving the disregulation of apoptosis include, but are not limited to, cardiovascular disease, cancer, and immunosuppression related disorders such as AIDS. An example of cardiovascular disease involving apoptosis is the cell death resulting in myocardial infarction. The methods described herein are thus useful in measuring the level of the isodipeptide in body fluids in order to mark the earliest onset of apoptosis following a heart attack. Additionally, it has now been found that the vast majority of immune cell death in AIDS patients occurs in cells which are not infected with the human immunodeficiency virus (HIV). Both infected and uninfected cells are now known to die by apoptosis.

Methods involving assessing the therapeutic modulation of apoptosis include, but are not limited to, testing for the appearance of the isodipeptide in order to evaluate the efficacy of treatment of heart attacks, chemotherapeutic and radiation treatment of cancers and AIDS treatments. The assay provides accurate quantitation of the levels of the isodipeptide which is directly correlated to the levels of apoptosis. Thus the effects of particular therapies on disease progression can be measured over time.

The invention can further be used to determine tissue-specific cell death so as to provide physicians with information regarding the relative levels of apoptosis in different tissues and organs. Levels of cell death in a target cell colony, such as tumors and other cancerous tissue can also be measured by the present invention. This is particularly useful in monitoring the success of chemotherapy.

The invention can further be adapted to a high throughput format for automation of assaying levels of apoptosis in patients. A suitable system for high throughput analysis is described in U.S. Pat. No. 5,037,207 (1991). The invention can also be used to measure red blood cell production for instance, treatments which induce anemia such as chemotherapy and dialysis.

The invention encompasses methods to measure thrombolysis and the effectiveness of therapy. The last stage of clot formation in the blood is cross-linking of fibrin by plasma transglutaminase (blood coagulation factor XIII). Naturally, fibrin cross-linking occurs when thrombi are formed either in deep vein thrombosis or in myocardial infarction. When these clots are lysed in well-defined therapeutic protocols, the proteolytic degradation of the cross-linked clot leads to the elevation of circulatory levels of the isodipeptide. Harsfalvi et al. (1992); and Harsfalvi et al. (1994) *Fibrinol.* 8:378–381.

The invention encompasses methods of monitoring levels of apoptosis associated with diseases or traumas to a target cell colony. Such diseases include, but are not limited to, Alzheimer's disease, Parkinson's disease and Pick's atrophy. Trauma includes, but is not limited to, damage, both physical, chemical or otherwise, to the central nervous system, including the brain, spinal cord and/or peripheral nerves. Assaying the isodipeptide in cerebrospinal samples is useful to evaluate the degree of apoptosis in the brain and the spinal cord.

Cell death in particular organs or tissues suitable for monitoring include, but are not limited to, cerebrospinal, cardiac, liver, lung, allogeneic transplantation tissues, gastrointestinal, reproductive, lymphoid tissues and malignancies.

Measurement of apoptosis can be repeated over time and the changes in the concentrations of the isodipeptide compared. Normally, an increase in the concentration of the isodipeptide indicates an increase in cell death and a decrease in the concentration of the isodipeptide indicates a decrease in cell death. These methods are particularly suited to monitoring disease progression and the effect of apoptosis-modulating agents.

The invention encompasses methods of monitoring the presence and effects of toxic environmental agents on animals. The isodipeptide is present in the blood plasma of male winter flounder and its concentration varies seasonally. Squires et al. (1980) *Biochem. J.* 185:761–766. Reports also indicate that a number of toxic agents in the environment can initiate apoptosis, measurement of isodipeptide concentration in extracellular fluids and the circulation of various species living in natural environments. The animals can be either in their native habitat or agricultural animals such as cattle, pigs and fish. In agricultural animals, the invention is particularly suitable for measuring levels of apoptosis related to stress such as that caused by overcrowding.

The invention further encompasses methods of measuring the protein-bound isodipeptide content in complex samples. In such instances the samples are exhaustively digested by proteolytic enzymes prior to measurement of the isodipeptide. Suitable methods for exhaustive proteolysis are known in the art and include, for instance, the method described by Fesus et al. (1985) *J. Biol. Chem.* 260:13771–17338. After proteolytic digestion, the isodipeptide is measured by the methods described herein. The importance of measuring protein-bound cross-links is clearly shown by the widespread occurrence and importance of this cross-link in stabilizing tissue structures (Greenberg et al. (1991) *FASEB J.* 5:3071–3077) and the recent efforts to modify meat and bread by introducing high levels of protein cross-linking by transglutaminase reactions. Motoki et al. (1983) *J. Food Sci.* 48:561–565; Nio et al. (1986) *Agric. Biol. Chem.* 50:1409–1412; and Friedman et al. (1990) *J. Agric. Food Chem.* 38:2011–2020.

Figure 3A:
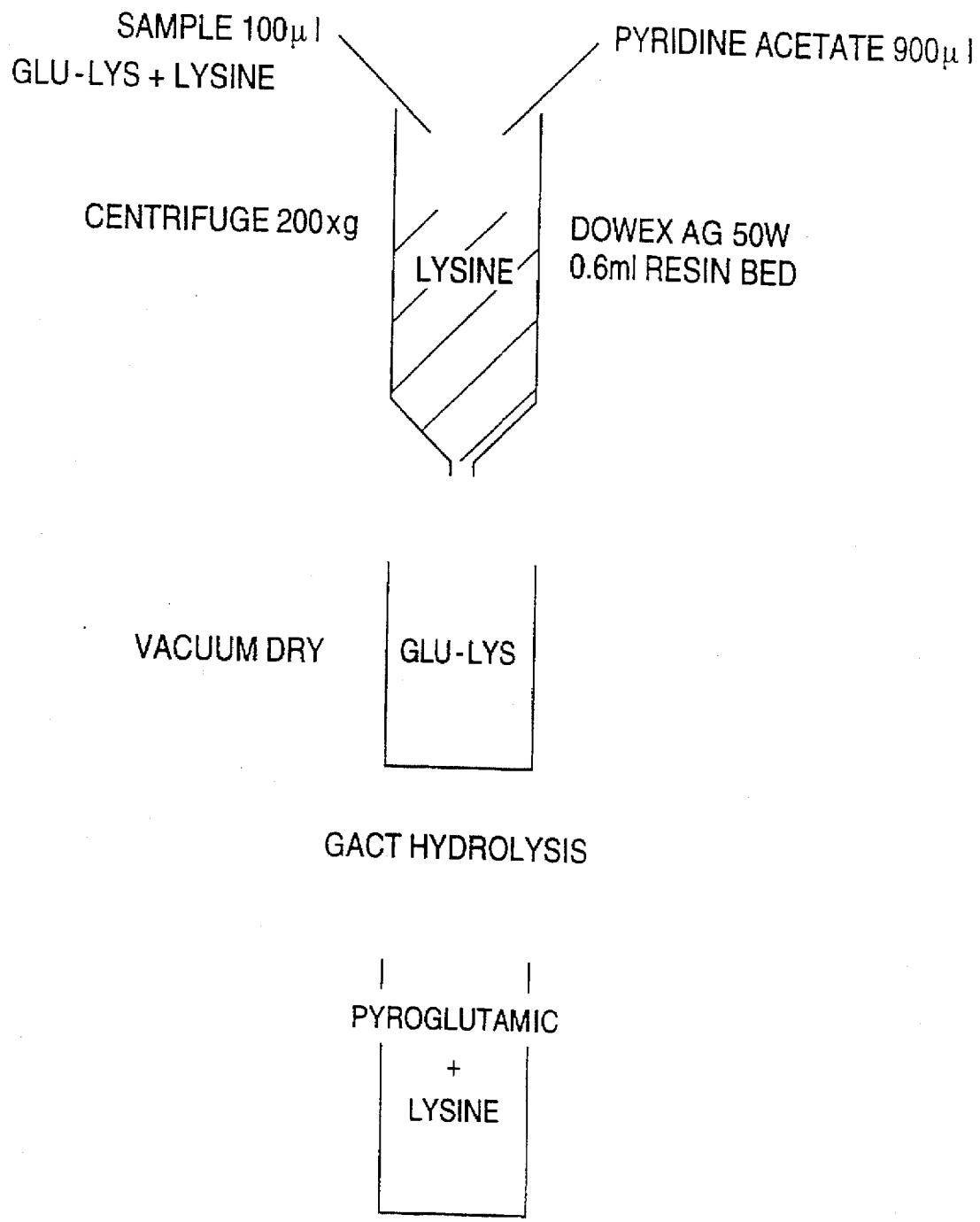
FIGS. 3A and 3B depict a reaction scheme of the method described in Example 3.
Figure 3B:
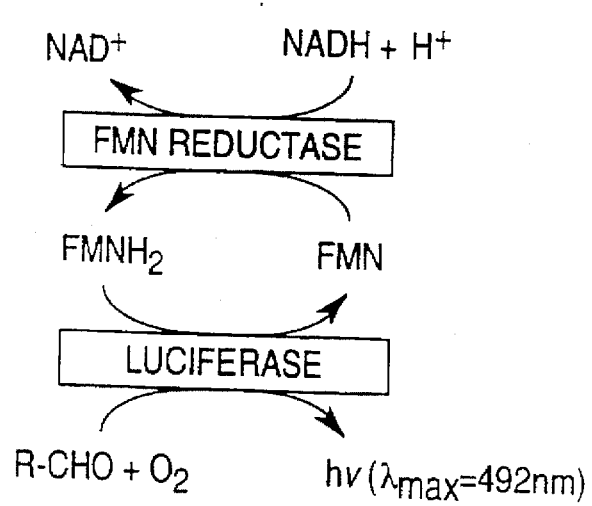

The present invention provides methods of measuring levels of apoptosis by quantitatively measuring the protein-derived isodipeptide. The methods comprise obtaining a sample, optionally diluting the sample in a suitable buffer, deproteinizing the sample if necessary, removing free lysine to form an isolate, hydrolyzing the isodipeptide to free amino acid residues, and quantitatively measuring the resulting free lysine. The basic reaction steps are depicted in FIGS. 3A and 3B.

The sample can be derived from any suitable physiological source. Suitable physiological samples for determination of apoptosis include, but are not limited to, saliva, serum, plasma, synovial fluid, urine, cerebrospinal fluid and ascites. Suitable complex samples include, but are not limited to, proteins, tissue cells from cell culture, food products and animal products. Preferably, the sample is serum for ease of use since serum has a lower protein concentration than plasma. Urine samples can be also used to monitor changes in isodipeptide concentration; the isodipeptide is filtrated into the urine. The isodipeptide level was determined in urine samples by the HPLC technique and values of between 5–40 μmol/L were found in healthy individuals. Generally, in the case of body fluids, cellular debris and proteins should be excluded or removed. Thus biological fluids from which cells can be removed, are preferred.

Deproteinization is necessary whenever protein levels in the sample exceed about 0.1 mg/mL. Typically, deproteinization is useful in plasma, urine, other body fluids and complex samples. Preferably plasma samples are deproteinized at 4° C. Deproteinization can be performed by any method known in the art. In one preferred embodiment, deproteinization is performed using the Centrifree centrifugal microseparator partition device according to the manufacturer's instructions (Amicon, cutoff molecular weight 5000). In another preferred embodiment, deproteinization is accomplished by precipitating the proteins in the sample, for instance with trichloroacetic acid and proteolytically digesting the isolate. Suitable enzymes which can be used for proteolytically digesting the precipitate include, for example, trypsin, chymotrypsin, and papain. Methods of protein precipitation and digestion are known in the art.

Preferably, the sample is placed in a vial or test tube which has a capacity of at least ten times the volume of the sample. The sample can be diluted prior to addition of the quantifiable agent. Any suitable buffer can be used, including, but not limited to, phosphate buffered saline (PBS), saline and Ringer's solutions. In the case of blood samples, an anticoagulant is preferably added prior to removing the free lysine in an amount effective to reduce or prevent coagulation. Preferably, trisodium citrate is added as an anticoagulant to a final concentration of about 108 mmol/L. Urine or other body fluid samples are collected without anticoagulant.

If necessary, when the isodipeptide content of proteins is analyzed, proteins can first be precipitated with trichloroacetic acid, washed with ether and dried. Samples are then subject to exhaustive proteolytic digestion, preferably, in morpholine buffer according to the method described by Fesus et al. (1985). Other suitable deproteinization methods include, but are not limited to, acidic or salt precipitation.

Free lysine is removed from the deproteinized sample. Suitable methods of removing lysine include, but are not limited to, ion exchange chromatography. Preferably, free lysine is removed by passing the sample over an AG-50W-X8 Dowex resin in pyridinium form. Other resins which would react similarly with free lysine can be used as well. Preferably the column is in a small volume, approximately 0.5 mL to 2 mL. The preferred volume is a 0.6 mL resin bed for 100 μL of sample volume. If the Dowex column is used, the sample should be eluted with an acidic buffer which is preferably volatile. The isodipeptide is eluted with 9–10 volumes of buffer at a pH of from 3.0 to 6.0., with a preferred pH of about 3.7. Suitable buffers include, but are not limited to, pyridine acetate, trimethylamine, and formic acid. In a preferred embodiment, 100 mM of pyridine acetate is used at a pH of 3.7. Under these conditions, lysine remains bound to the column and the isodipeptide is eluted free of non-bound lysine. Preferably the column is centrifuged to maximize recovery.

After free lysine is removed, the sample is preferably dried. Drying can be by any method, including, but not limited to, air-drying, freeze drying, drying at elevated temperatures up to about 50° C., and vacuum drying. Due to the stability of the purified isodipeptide, the method of drying is not critical except temperature.

The dried sample is then resuspended in an amount of a buffer suitable for subsequent hydrolysis. Typically, the volume is about one-third that of the deproteinized sample prior to removal of lysine. For instance, if 100 μL were loaded on the column, it would be resuspended at this step in 30 μL of a suitable buffer. Typical suitable buffers include, but are not limited to, phosphate, Tris-HCl. Preferably, the buffer is 5 mM sodium phosphate buffer, pH 7.5.

The isodipeptide is then hydrolyzed to free amino acid residues. Any method of hydrolysis known in the art is suitable provided it releases free lysine residues from the isodipeptide in a quantifiable form. Preferably, the isodipeptide is enzymatically hydrolyzed to lysine and pyroglutaminic acid by the enzyme γ-glutamylamine cyclotransferase (GACT) which acts as a catalyst to improve the rate and efficiency of hydrolysis. GACT is purified from rabbit kidney, according to the method described by Fink et al. (1983).

Any effective concentration of GACT may be used. Typically, to achieve maximum reaction rates, the final concentration is 0.05 U/mL to 8 U/mL, preferably, the final concentration is 0.05 U/mL to 0.5 U/mL, more preferably the final concentration is 0.05 U/mL to 0.15 U/mL. Most preferably, 0.1 U/mL final concentration is used. The reaction is typically carried out at about 37° C. for 2 hours. Reaction times may vary depending on the enzyme concentration but can be easily determined empirically.

The free lysine residues are then quantitated in the hydrolyzed sample. Any method of quantitating lysine can be used. Such methods include, but are not limited to, fluorescence derivatization, PITC derivatization and generation of luminescence signal. Preferably the sample is reacted with Saccharopine dehydrogenase, NADH and α-ketoglutarate according to the method described by Nakatani et al. (1972) Anal. Biochem. 49:225–231 to produce saccharopine. As a representative example, the total volume of a 100 μL reaction mix includes:

a. 30 μL of 5 mM sodium phosphate buffer to resuspend the dried sample;

b. 20 μL of partially purified GACT solution collected at the end of purification;

c. 50 μL of 50 mM Tris buffer 6.8 pH containing:
Saccharopine dehydrogenase (Sigma) 10 U/mL,
NADH 0.4 mM, and
α-ketoglutarate 0.4 mM.

After the reaction, the samples are placed on ice to stop the reaction and to reduce spontaneous oxidation of NADH. The bioluminescence is then measured according to the method described by Fosse et al. (1986) J. Neurochem. 47(2):340–349. Briefly, the sample is diluted approximately 10 fold in potassium phosphate buffer, pH 7.0, an aliquot of the diluted sample is added to the bioluminescent reaction mixture and the luminescence is measured in a luminometer at 492 nm. The bioluminescence measurement must be made within 30 minutes of stopping the reaction.

Figure 2A:
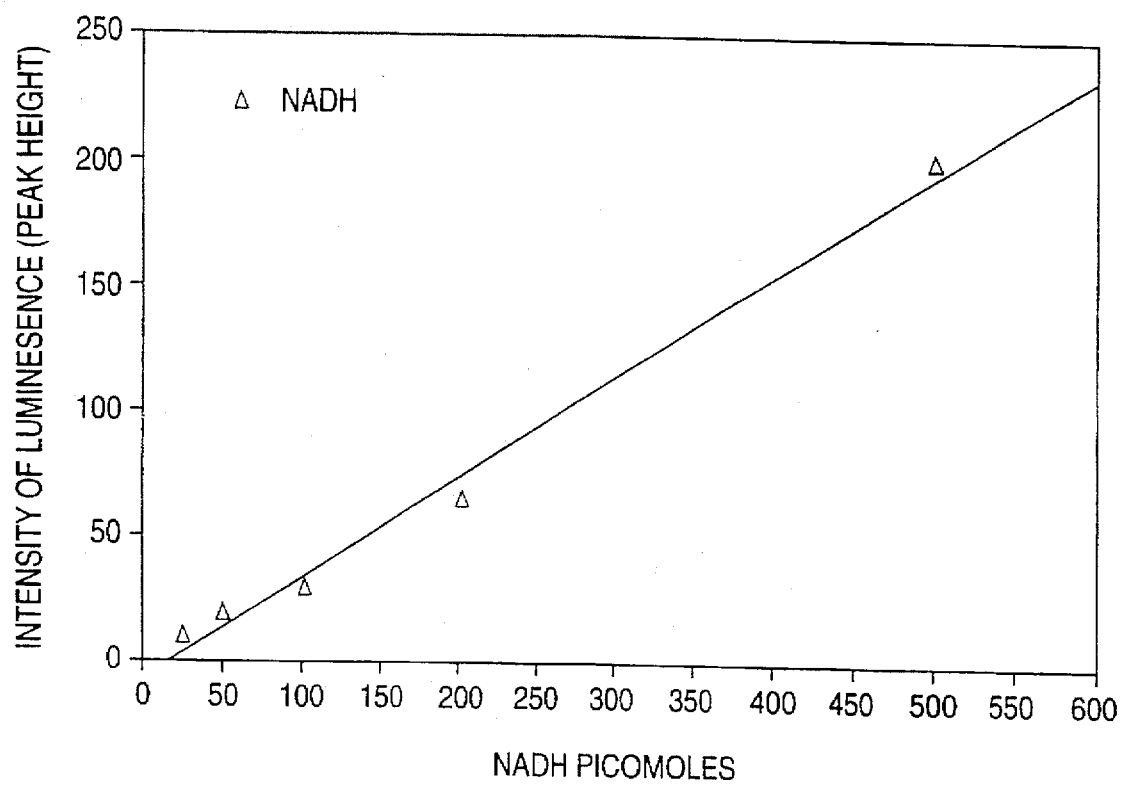
FIG. 2A is a graph depicting an NADH calibration curve.
Figure 2B:
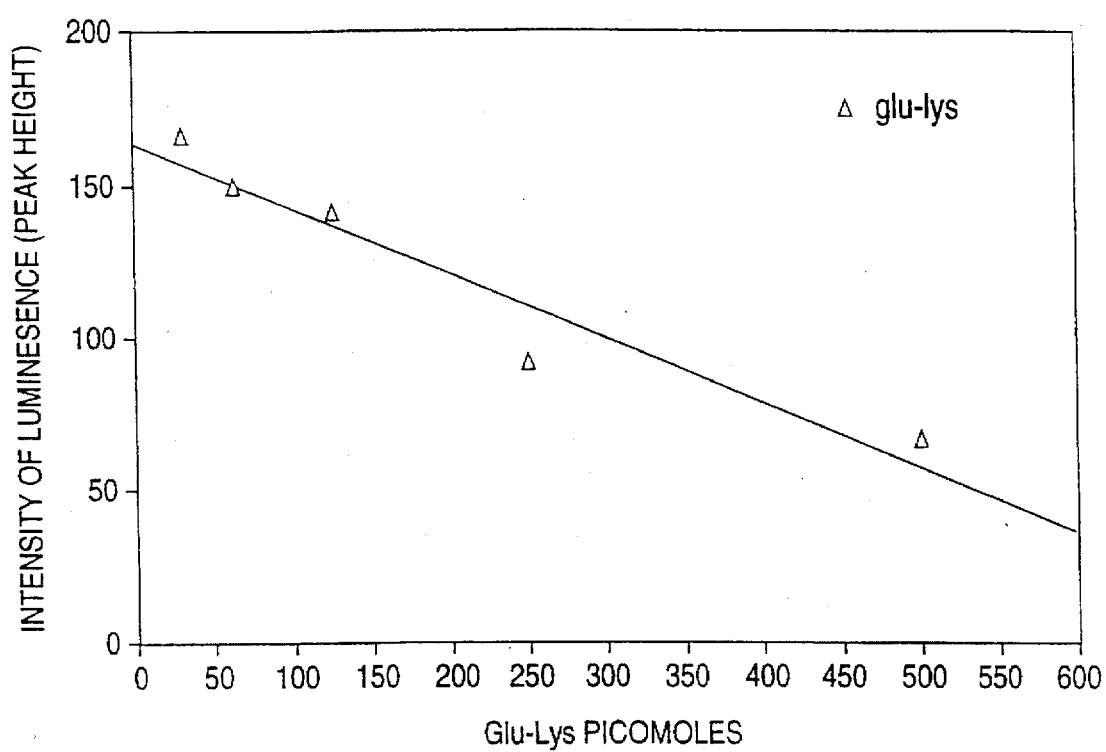
FIG. 2B is a graph depicting a glutamyl lysine calibration curve.

The luminescence obtained is then compared to a standard graph prepared using known concentrations of the isodipeptide to determine the isodipeptide concentration of the original sample. Such graphs are readily prepared, for instance, as described in the Examples below. Representative graphs are depicted in FIGS. 2A and 2B.

The invention further provides a kit having a suitable container for measuring the level of the isodipeptide in a sample in vitro. Such a kit is suitable for use in any of the applications described herein. The kit may also include a physiologically acceptable buffer for diluting the sample, and reagents for deproteinization, removal of lysine, hydrolysis of the isodipeptide and measurement of free lysine. Additional components may be included, these include, but are not limited to, means for measuring the amount of quantifiable agent.

The following examples are provided to illustrate but not limit the invention.

EXAMPLE 1

Prior Art Methods Correlating Serum Isodipeptide with Apoptosis in HIV-positive Individuals Peripheral blood was obtained from 50 HIV-infected individuals from the Service for Infectious Diseases (Pr. R. Rouè), Bégin Military Hospital, Saint Mandé, France. Thirty seven individuals were clinically asymptomatic (stage II of the Center for Disease Control ($CDC^3$ Atlanta classification)), and twelve were CDC stage IV. Control samples were obtained from HIV-seronegative healthy donors.

Peripheral blood mononuclear cells (PBMC) were isolated by Ficoll-Hypaque (Pharmacia, Sweden) centrifugation of heparinized blood from healthy donors and HIV-seropositive individuals. The cells were washed with RPMI medium and, in some experiments, cultured to a density of $1\times10^6$/mL in complete medium composed of RPMI 1640 supplemented with 10% v/v heat-inactivated FCS, 2 mM L-glutamine (Gibco-Europe, Karlsruhe, FRG), penicillin at 50 U/mL and streptomycin at 50 µg/mL in 25 $cm^2$ flasks. Cell culture media and plastic were from ICN-Flow (U.K.).
Evaluation of tissue transglutaminase The percentage of pre-apoptotic cells was evaluated by counting the tissue transglutaminase positive cells showing the typical apoptotic morphology as well as the apoptotic ghosts scored at the light microscopy (Laborlux D, Leitz, Wetzlar, Germany) over 1,000 total cells (including apoptotic ones).
DNA Nick End Labelling of lymph node sections TdT-mediate dUTP-biotin nick end labelling (TUNEL) was performed on paraffin embedded sections as described by Gavrieli et al. (1992) *J. Cell Biol.* 119:493–501 with few modifications. Endogenous peroxidase was inactivated using 3% $H_2O_2$ for 15 minutes at room temperature, slides were then incubated in terminal deoxynucleotidyl transferase (TDT) buffer containing: 0.5 e.U/µL TDT, 0.25 nmol/µL biotinylated-d-UTP, 2.5 mM $CoCl_2$, for 60 minutes at 37° C. in a humid atmosphere. The reaction was terminated by transferring the slides to TB buffer containing 300 mM NaCl, 30 mM sodium citrate, for 15 minutes at room temperature. The cells were rinsed in distilled water, covered with 2% aqueous solution of bovine serum albumin (BSA) for 10 minutes, then immersed in PBS for 5 minutes. The slides were covered with peroxidase conjugated streptavidin (BioGenex, San Ramon, Calif.), incubated for 20 minutes and stained with DAB (3-3' diaminobenzidine tetrahydrochloride) for 5–10 minutes.
ε(γ-glutamyl)lysine measurement Plasma samples were deproteinized using Centrifree partition device (Amicon) with a molecular weight cut-off of 5,000. Briefly, ε(γ-glutamyl)lysine measurement was carried out as follows. A preliminary purification of amino acids and peptides was achieved by eluting aliquots of plasma samples on ion-exchange chromatography and on silica columns. The eluate was derivatized with PITC and separation of amino acids and peptide derivatives by HPLC on a µBundapack C18 column $^3$H-labelled ε(γ-glutamyl)lysine was used as an internal standard throughout the procedure. The elution position of the isodipeptide was established by standard ε(γ-glutamyl)lysine (Serva). The quantification of ε(γ-glutamyl)lysine in the plasma was based on the peak area as compared to the peaks obtained using a standard amount of the isodipeptide and on the recovery determined from the isotope dilution.
Cell death analysis by flow cytometry Quantification of apoptosis was carried out on PBMC obtained from both healthy donors and seropositive individuals by stained with propidium iodide (PI), as described in Nicoletti et al. (1991) *J. Immunol. Meth.* 139:271–279. One million cells were suspended in 0.5 µL of staining solution (50 µg/mL PI, 0.1% sodium citrate, 0.1% Triton X-100). The samples were placed at 4° C. in the dark overnight before flow-cytometric analysis. Fluorescence was analyzed by flow cytometry using a FACSan II Analyzer (Becton Dickinson).

Figure 1B:
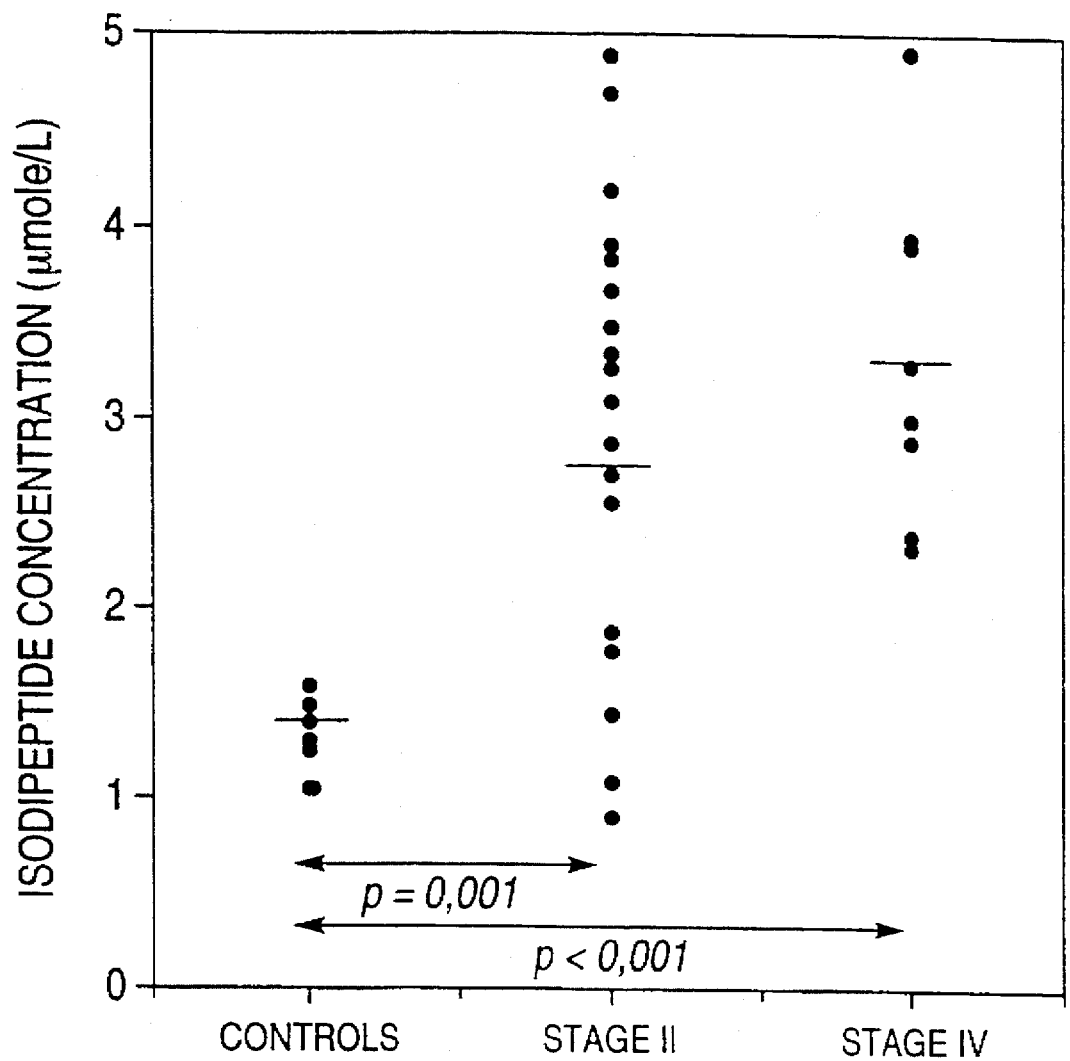

The results depicted in FIG. 1 indicate that isodipeptide levels found in serum can be directly correlated to HIV-related in vivo apoptosis.

EXAMPLE 2

Luminescence Calibration Method

The intensity of luminescence (measured by peak height) corresponds to the NADH concentration in a sample, that is the decrease in luminescence as compared to blank is the measure of lysine released which is directly related to the concentration of isodipeptide in the sample. Since the linear range of the NADH bioluminescence assay is between 10 to 1000 pmoles, the NADH calibration curve is built on 5 standards: 25, 50, 100, 200 and 500 pmoles. FIG. 2A. The upper concentration of 500 pmoles corresponds to the amount of NADH in 25 µL of the 1 mL diluted sample after the saccharopine dehydrogenase step. Therefore, this is the maximal luminescence value obtained when there is no isodipeptide present in the starting sample, no lysine is released by GACT and no NADH is consumed.

A second calibration curve is built on 5 concentrations of the isodipeptide in the 1–20 nmoles range having this amount in the 30 µL sodium phosphate solution to which GACT is added. The highest amount (20 nmoles) corresponds to 500 pmoles in the 25 µL added to the bioluminescence reaction mixture and, as expected, consumes the highest amount of NADH. FIG. 2B. The isodipeptide concentration in the original sample is calculated based on such calibration curves taking into account dilutions and volume of original sample for obtaining final results.

EXAMPLE 3

Blood Sample Preparation

2000 µL human blood was taken by syringe into polypropylene tubes. Trisodium citrate was added as anticoagulant to a final concentration of 108 mmol/L and the plasma was decanted into a separate tube after coagulation occurred.

Plasma samples and protein digests were then deproteinized at 4° C. Deproteinization was performed using the Centrifree centrifugal microseparator partition device according to the manufacturer's instructions (Amicon, cut off molecular weight 5000).

Free lysine was removed using a small column (0.6 mL resin bed) filled with AG 50W-X8 Dowex resin in pyridinium form. 100 µL of deproteinized sample was loaded onto the column and the isolate was eluted with 900 µL 100 mM pyridine acetate buffer, pH 3.7. To maximize the recovery of isodipeptide, the column was centrifuged (200 g) for 10 minutes at room temperature. The eluate was then vacuum dried. The dried sample contained the isodipeptide and some acidic amino acids.

The sample was then resuspended in 30 µL 5 mM sodium phosphate buffer pH 7.5. Hydrolysis was carried out at 37° C. for 2 hours using 20 µL purified GACT (0.1 U/mL final concentration). GACT was isolated, and units of activity were assigned according to the method described by Fink et al. (1993).

50 µL of 50 mM Tris-HCl buffer, pH 6.8 containing Saccharopine dehydrogenase (Sigma) 10 U/mL, NADH (Sigma) 400 nmoles/mL, α-ketoglutarate 400 nmoles/L was added to the GACT hydrolyzed sample. The samples were incubated at 25° C. for 3 hours in the dark. The samples were then placed on ice. The bioluminescence measurement was made within 30 minutes.

The sample was diluted to 1 mL using 50 mM potassium phosphate buffer, pH 7.0 (PPB), then 25 µL of the diluted sample was added to 100 µL of the bioluminescent reaction mixture and the luminescence reaction was measured in a luminometer (LKB 1251). The bioluminescent reaction mixture consisted of:

| | |
|---|---|
| PPB filtered through a 0.45 µm filter | 10 mL |
| Luciferase (Serva, stock solution 10 mg/mL) | 10 µL |
| FMN reductase* (stock solution 2.5 mg/10 mL distilled water) | 200 µL |
| FMN* (stock solution 2.5 mg/10 mL distilled water) | 100 µL |
| Tetradecanal* (stock solution 4.25 mg/10 mL distilled water) | 200 µL |

*obtained from Boehringer Mannheim

The concentration of isodipeptide was calculated according to an NADH standard curve and the various dilutions made during the assay.

Using the method described herein, in one plasma sample, a value of 4.7±0.8 µmol/L was found in ten separate measurements. These results demonstrate very good reproducibility. Applying the same technique to protein samples, the protein-bound ε(γ-glutamyl)lysine cross-link was determined after proteolytic digestion in newborn rat epidermis: repeated measurements yielded 8–10 nmol/mg protein. These results also agree with values obtained using the chromatography methods.

EXAMPLE 4

Tissue or Cell Culture Sample Preparation

Protein samples are obtained from mammalian tissue samples, cell culture preparations or other suitable sources, including, but not limited to, food proteins. Protein samples are first precipitated with 15% trichloracetic acid, washed with ether and dried in air. Suitable sample sizes of protein range from 1 to 3 mg/mL. Samples are then subject to exhaustive proteolytic digestion in 1.0 mL morpholine buffer according to the method described by Fesus et al. (1985).

Protein digests are then deproteinized at 4° C. Deproteinization is performed using the Centrifree centrifugal microseparator partition device according to the manufacturer's instructions (Amicon, cut off molecular weight 5000). The samples are then treated as described in Example 3.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention which is delineated by the appended claims.

What is claimed is:

1. A method of measuring the amount of protein-derived isodipeptide in a sample comprising the steps of:
   a) obtaining the sample;
   b) removing free lysine from the sample to form an isolate;
   c) hydrolyzing the isolate to release free lysine and
   d) measuring the free lysine,
   wherein the concentration of free lysine obtained from step c) is directly related to the amount of isodipeptide in the sample and further wherein the method is capable of detecting an amount of isodipeptide of about 25 pmoles.

2. The method according to claim 1 wherein the sample is diluted in a suitable buffer prior to step b).

3. The method according to claim 2 wherein the buffer is selected from the group consisting of phosphate buffered saline, saline, and Ringer's solution.

4. The method according to claim 1 or 2, wherein the sample contains proteins and is deproteinized prior to step b).

5. The method according to claim 1 wherein the sample is a physiological sample.

6. The method according to claim 5 wherein the physiological sample is selected from the group consisting of saliva, blood, serum, plasma, synovial fluid, urine, cerebrospinal fluid and ascites.

7. The method according to claim 6 wherein the sample is blood and the method further comprises the step of adding an anticoagulant prior to step b).

8. The method according to claim 7, wherein the anticoagulant is added to a final concentration of 108 mmol/L.

9. The method according to claim 1 wherein the sample is a complex sample.

10. The method according to claim 9 wherein the complex sample is selected from the group consisting of proteins, food products and animal products.

11. The method according to claim 1 wherein step b) comprises the steps of:
    i) passing the sample over an AG-50W-X8 Dowex resin in pyridinium form; and
    ii) eluting the sample with an acidic buffer.

12. The method according to claim 11 wherein the acidic buffer is selected from the group consisting of pyridine acetate, trimethylamine, and formic acid.

13. The method according to claim 1 wherein hydrolysis is catalyzed by the enzyme γ-glutamylamine cyclotransferase (GACT).

14. The method according to claim 13 wherein the γ-glutamylamine cyclotransferase is in an amount of from about 0.05 U/mL to 8 U/mL.

15. The method according to claim 1 wherein step d) further comprises the steps of:

i) reacting the hydrolyzed isolate with saccharopine dehydrogenase, NADH and α-ketoglutarate; and ii) measuring luminescence at 490 nm to determine the remaining amount of NADH, wherein the decrease in NADH is directly related to the initial concentration of the isodipeptide.

* * * * *